US009522872B2

(12) United States Patent
Seyedi et al.

(10) Patent No.: US 9,522,872 B2
(45) Date of Patent: Dec. 20, 2016

(54) METHODS FOR SYNTHESIZING SUBSTITUTED TETRACYCLINE COMPOUNDS

(75) Inventors: Farzaneh Seyedi, Mansfield, MA (US); Tadeusz Warchol, Northborough, MA (US); Mark Grier, Medford, MA (US)

(73) Assignee: PARATEK PHARMACEUTICALS, INC., Boston, MA (US)

( * ) Notice: Subject to any disclaimer, the term of this patent is extended or adjusted under 35 U.S.C. 154(b) by 1003 days.

(21) Appl. No.: 12/217,709

(22) Filed: Jul. 7, 2008

(65) Prior Publication Data

US 2009/0156842 A1    Jun. 18, 2009

Related U.S. Application Data

(60) Provisional application No. 61/060,351, filed on Jun. 10, 2008, provisional application No. 60/948,385, filed on Jul. 6, 2007.

(51) Int. Cl.
*C07C 237/12* (2006.01)
*C07C 231/12* (2006.01)

(52) U.S. Cl.
CPC ......... C07C 231/12 (2013.01); *C07C 2103/44* (2013.01)

(58) Field of Classification Search
USPC .................................. 514/152; 552/203, 205
See application file for complete search history.

(56) References Cited

U.S. PATENT DOCUMENTS

| | | |
|---|---|---|
| 2,820,824 A | 1/1958 | Weidenheimer et al. |
| 2,980,584 A | 4/1961 | Hammer ......................... 167/65 |
| 2,990,331 A | 6/1961 | Neumann et al. ............... 167/65 |
| 3,062,717 A | 11/1962 | Hammer ......................... 167/65 |
| 3,165,531 A | 1/1965 | Blackwood et al. ...... 260/330.5 |
| 3,304,227 A | 2/1967 | Loveless |
| 3,454,697 A | 7/1969 | Joyner et al. .................. 424/227 |
| 3,557,280 A | 1/1971 | Weber et al. ................... 424/80 |
| 3,674,859 A | 7/1972 | Beutel .............................. 424/80 |
| 3,876,699 A | 4/1975 | Nager et al. |
| 3,957,980 A | 5/1976 | Noseworthy .................. 424/227 |
| 4,018,889 A | 4/1977 | Armstrong ....................... 424/80 |
| 4,024,272 A | 5/1977 | Rogalski et al. .............. 424/275 |
| 4,126,680 A | 11/1978 | Armstrong ........................ 424/80 |
| 4,666,897 A | 5/1987 | Golub et al. |
| 4,704,383 A | 11/1987 | McNamara et al. |
| 4,925,833 A | 5/1990 | McNamara et al. |
| 4,935,412 A | 6/1990 | McNamara et al. |
| 5,258,371 A | 11/1993 | Golub et al. |
| 5,308,839 A | 5/1994 | Golub et al. |
| 5,321,017 A | 6/1994 | Golub et al. |
| RE34,656 E | 7/1994 | Golub et al. |
| 5,459,135 A | 10/1995 | Golub et al. |
| 5,523,297 A | 6/1996 | Pruzanski et al. |
| 5,532,227 A | 7/1996 | Golub et al. |
| 5,668,122 A | 9/1997 | Fife et al. |
| 5,770,588 A | 6/1998 | McNamara et al. |
| 5,773,430 A | 6/1998 | Simon et al. |
| 5,789,395 A | 8/1998 | Amin et al. |
| 5,827,840 A | 10/1998 | Ramamurthy et al. |
| 5,834,449 A | 11/1998 | Thompson et al. |
| 5,834,450 A | 11/1998 | Su |
| 5,837,696 A | 11/1998 | Golub et al. |
| 5,843,925 A | 12/1998 | Backer et al. |
| 5,919,774 A | 7/1999 | Bach et al. |
| 5,919,775 A | 7/1999 | Amin et al. |
| 5,929,055 A | 7/1999 | Ryan et al. |
| 5,977,091 A | 11/1999 | Nieman et al. |
| 5,998,390 A | 12/1999 | Ramamurthy et al. |
| 6,015,804 A | 1/2000 | Golub et al. |
| 6,043,225 A | 3/2000 | Shor et al. |
| 6,043,231 A | 3/2000 | Pruzanski et al. |
| 6,100,248 A | 8/2000 | Golub et al. |
| 6,231,894 B1 | 5/2001 | Stamler et al. |
| 6,277,061 B1 | 8/2001 | Golub et al. |
| 6,500,812 B2 | 12/2002 | Nelson et al. ................. 514/152 |
| 6,617,318 B1 | 9/2003 | Nelson et al. ................. 514/152 |
| 6,624,168 B2 | 9/2003 | Nelson et al. ............. 514/252.1 |
| 6,642,270 B2 | 11/2003 | Nelson et al. ................. 514/464 |
| 6,683,068 B2 | 1/2004 | Nelson et al. ................. 514/152 |
| 6,818,634 B2 | 11/2004 | Nelson et al. ................. 514/152 |
| 6,818,635 B2 | 11/2004 | Nelson et al. ................. 514/152 |
| 6,833,365 B2 | 12/2004 | Levy et al. ..................... 514/152 |
| 6,846,939 B2* | 1/2005 | Nelson et al. ................. 552/205 |
| 6,849,615 B2 | 2/2005 | Nelson et al. ................. 514/152 |
| 6,908,939 B2* | 6/2005 | Bernardon et al. ............ 514/369 |
| 7,001,918 B2 | 2/2006 | Huss et al. ..................... 514/427 |
| 7,067,681 B2 | 6/2006 | Nelson et al. ................. 552/206 |
| 7,094,806 B2 | 8/2006 | Nelson et al. ................. 514/471 |

(Continued)

FOREIGN PATENT DOCUMENTS

WO    WO-0119784 A1    3/2001
WO    WO-0204406 A2    1/2002

(Continued)

OTHER PUBLICATIONS

Bernd Giese et al. (abstract, Tetrahederon Letters (vol. 30, Issue 6, 1989, pp. 681-684).*
Ballestri et al. (J. Org. CHem. 1991, 56, 678-683).*
Pri-Bar et al. (Can. J. Chem., vol. 68, pp. 1544-1547 (1990).*
Nelson et al. (AN 2003:777531, HCAPLUS, DN 139:292094, abstract of WO 2003079984).*
Hashimoto et al., "Design and synthesis of complementing ligands for mutant thyroid hormone receptor TRβ(R320H): a tailor-made approach toward the treatment of resistance to thyroid hormone", *Bioorg. Med. Chem.*, 13(11):3627-3639 (2005).
Berge et al. "Pharmaceutical Salts." *J. Pharm. Sci.* 66.1(1977):1-19.
Chandler et al. "Matrix Metalloproteinases, Tumor Necrosis Factor and Multiple Sclerosis: An Overview." *J. Neuroimmunol.* 72(1997):155-161.
Dörwald. *Side Reactions in Organic Synthesis.* Wiley-VCH. (2005):IX.
Greenwald et al. "In Vitro Sensitivity of the Three Mammalian Collagenases to Tetracycline Inhibition: Relationship to Bone and Cartilage Degradation." Bone. 22.1(1998):33-38.

(Continued)

*Primary Examiner* — Sabiha N Qazi
(74) *Attorney, Agent, or Firm* — McCarter & English, LLP; Elizabeth A. Hanley

(57) ABSTRACT

Methods of synthesizing substituted tetracycline compounds are provided.

14 Claims, No Drawings

(56) References Cited

U.S. PATENT DOCUMENTS

| | | | |
|---|---|---|---|
| 7,202,235 B2 | 4/2007 | Levy et al. .................... 514/152 |
| 7,208,482 B2 | 4/2007 | García-Luzón et al. ..... 514/152 |
| 7,326,696 B2 | 2/2008 | Nelson et al. |
| 7,553,828 B2 | 6/2009 | Nelson et al. |
| 7,595,309 B2 * | 9/2009 | Nelson et al. ................ 514/152 |
| 7,696,186 B2 | 4/2010 | Nelson et al. |
| 7,696,187 B2 | 4/2010 | Nelson et al. |
| 7,820,641 B2 * | 10/2010 | Nelson et al. ................ 514/152 |
| 7,858,601 B2 * | 12/2010 | Berniac et al. ............... 514/152 |
| 8,048,867 B2 * | 11/2011 | Nelson et al. ................ 514/152 |
| 8,946,196 B2 * | 2/2015 | Johnston ............... C07C 231/12 514/152 |
| 9,090,541 B2 * | 7/2015 | Viski .................... C07C 237/26 |
| 2003/0125348 A1 | 7/2003 | Nelson et al. |
| 2004/0138183 A1 | 7/2004 | Nelson et al. ................ 514/152 |
| 2004/0157807 A1 | 8/2004 | Levy ............................ 514/152 |
| 2004/0176334 A1 | 9/2004 | Nelson et al. ................ 514/152 |
| 2004/0214801 A1 | 10/2004 | Nelson et al. ................ 514/152 |
| 2004/0266740 A1 | 12/2004 | Huss et al. .................... 514/152 |
| 2005/0026875 A1 | 2/2005 | Nelson et al. ................ 514/152 |
| 2005/0026876 A1 | 2/2005 | Nelson et al. ................ 514/152 |
| 2005/0038002 A1 * | 2/2005 | Nelson et al. ................ 514/152 |
| 2005/0119235 A1 | 6/2005 | Nelson et al. ................ 514/152 |
| 2005/0137174 A1 | 6/2005 | Ohemeng et al. ............ 514/152 |
| 2005/0143352 A1 | 6/2005 | Nelson et al. ................ 514/152 |
| 2005/0143353 A1 | 6/2005 | Nelson et al. ................ 514/152 |
| 2005/0187198 A1 | 8/2005 | Nelson et al. ................ 514/152 |
| 2005/0250744 A1 | 11/2005 | Levy et al. ................... 514/152 |
| 2005/0288262 A1 | 12/2005 | Bandarage et al. .......... 514/152 |
| 2006/0003971 A1 | 1/2006 | Nelson .......................... 514/152 |
| 2006/0084634 A1 | 4/2006 | Huss et al. .................... 514/152 |
| 2006/0148765 A1 | 7/2006 | Nelson et al. ................ 514/152 |
| 2006/0166944 A1 | 7/2006 | Berniac et al. ............... 514/152 |
| 2006/0166945 A1 | 7/2006 | Abato et al. .................. 514/152 |
| 2006/0205698 A1 | 9/2006 | Nelson et al. ................ 514/152 |
| 2006/0229282 A1 | 10/2006 | Nelson et al. ................ 514/152 |
| 2006/0234988 A1 | 10/2006 | Nelson et al. ................ 514/152 |
| 2006/0281717 A1 | 12/2006 | Berniac et al. ............... 514/152 |
| 2006/0287283 A1 | 12/2006 | Amoo et al. |
| 2007/0072834 A1 | 3/2007 | Nelson et al. ................ 514/152 |
| 2007/0093455 A1 | 4/2007 | Abato et al. .................. 514/114 |
| 2008/0015169 A1 | 1/2008 | Nelson et al. |
| 2008/0287401 A1 | 11/2008 | Johnston et al. |
| 2009/0306022 A1 | 12/2009 | Nelson et al. |
| 2009/0325908 A1 | 12/2009 | Nelson et al. |
| 2010/0113400 A1 | 5/2010 | Nelson et al. |
| 2010/0113401 A1 | 5/2010 | Johnston et al. |
| 2010/0160263 A1 | 6/2010 | Nelson et al. |
| 2012/0283201 A1 | 11/2012 | Nelson et al. |
| 2015/0265635 A1 * | 9/2015 | Viski .................... C07C 237/26 514/152 |

FOREIGN PATENT DOCUMENTS

| | | |
|---|---|---|
| WO | WO-0204407 A2 | 1/2002 |
| WO | WO-02072532 A1 | 9/2002 |
| WO | WO-03075857 A2 | 9/2003 |
| WO | WO-2004091513 A2 | 10/2004 |
| WO | WO 2005/009943 A2 | 2/2005 |
| WO | WO 2005/075439 A1 | 8/2005 |
| WO | WO 2007/014154 A2 | 2/2007 |
| WO | WO-2008134048 A2 | 11/2008 |

OTHER PUBLICATIONS

Li et al. "Immunological Characterization of Cell-Surface and Soluble Forms of Membrane Type 1 Matrix Metalloproteinase in Human Breast Cancer Cells. and in Fibroblasts." *Mol. Carcinog.* 22(1998):84-94.

Liedtke et al. "Effective Treatment of Models of Multiple Sclerosis by Matrix Metalloproteinase Inhibitors." *Ann. Neurol.* 44(1998):35-46.

Ryan et al. "Potential of Tetracyclines to Modify Cartilage Breakdown in Osteoarthritis." *Curr. Opin. Rheumatol.* 8(1996):238-247.

Stetler-Stevenson et al. "Tumor Cell Interactions With the Extracellular Matrix During Invasion and Metastasis." *Annu. Rev. Cell Biol.* 9(199):541-573.

Tryggvason et al. "Proteolytic Degradation of Extracellular Matrix in Tumor Invasion." *Biochim. Biophys. Acta.* 907(1987):191-217.

Van den Bogert et al. "Doxycycline in Combination Chemotherapy of a Rat Leukemia." *Cancer Res.* 48(1988):6686-6690.

Waitz. "Methods for Dilution Antimicrobial Susceptibility Tests for Bacteria That Grow Aerobically." *Natl. Comm. Clin. Lab. Standards.* Document M7-A2. 10.8(1990):13-20.

Zhang et al. "Coupling Reaction of Aryl Halides or Triflates With Amines Catalyzed by Palladium and Other Transition Metal." *Chinese J. Org. Chem.* 22.10(2002):685-693. (English Abstract Only).

U.S. Appl. No. 13/312,291, Nelson et al.

\* cited by examiner

METHODS FOR SYNTHESIZING SUBSTITUTED TETRACYCLINE COMPOUNDS

RELATED APPLICATIONS

This non-provisional patent application claims priority under 35 U.S.C. §119(e) to the following provisional applications: U.S. Provisional Patent Application Ser. No. 60/948,385, filed Jul. 6, 2007, and U.S. Provisional Patent Application Ser. No. 61/060,351, filed Jun. 10, 2008, each of which is herein incorporated by reference in its entirety.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and Salmonella). The rise of tetracycline-resistant organisms has resulted in a general decline in use of tetracyclines and tetracycline analogue compositions as antibiotics of choice.

SUMMARY OF THE INVENTION

The invention generally pertains to methods for synthesizing substituted tetracycline compounds. In one embodiment, the invention pertains, at least in part, to a method for synthesizing a carboxaldehyde substituted tetracycline compound by reacting a tetracycline reactive intermediate under appropriate conditions with carbon monoxide, a palladium catalyst, a phosphine ligand, a silane and a base, such that the carboxaldehyde substituted tetracycline compound is synthesized. In some embodiments, the carboxaldehyde substituted tetracycline compound is a 7-, 9- and/or 10-carboxaldehyde substituted tetracycline compound.

For example, the tetracycline reactive intermediate is a halogenated tetracycline intermediate or a triflate substituted tetracycline intermediate. Examples include an iodine substituted tetracycline intermediate, a chlorine substituted tetracycline intermediate, a bromine substituted tetracycline intermediate, an iodine and chlorine substituted tetracycline intermediate or a bromine and iodine substituted tetracycline intermediate. In one embodiment, the compound is a 10-triflate substituted tetracycline intermediate. Other typical intermediates include 7-iodosancycline, 9-iododoxycycline, 7-chloro-9-iodosancycline or 7-bromo-9-iodosancycline.

In one embodiment, the method further comprises the step of precipitating the carboxaldehyde substituted tetracycline compound in a solvent, such as a non-polar solvent. Examples of non-polar solvents include diethyl ether, MBTE, heptane and combinations thereof.

In some embodiments, the method also includes further reacting the carboxaldehyde substituted tetracycline compound under palladium catalyzed coupling conditions, hydrogenolysis conditions or reductive amination conditions.

In another embodiment, the invention pertains, at least in part, to a method for synthesizing a substituted tetracycline compound comprising reacting a reactive tetracycline intermediate with carbon monoxide, a palladium catalyst, a phosphine ligand, a silane and a base under appropriate conditions, wherein the reactive tetracycline intermediate is substituted at a first position with a first reactive moiety and substituted at a second position with a second reactive moiety, such that the first reactive moiety is replaced with a carboxaldehyde substituent and the second reactive moiety is unreacted. Typically, the first and second reactive moieties are selected from halogens and triflates. For example, the first reactive moiety is iodine and the second reactive moiety is bromine. In one embodiment, the reactive tetracycline intermediate is 7-bromo-9-iodosancycline.

In one embodiment, the method further comprises the step of precipitating the carboxaldehyde substituted tetracycline compound in a solvent, such as a non-polar solvent. Examples of non-polar solvents include diethyl ether, MBTE, heptane and combinations thereof.

In some embodiments, the method further comprises the step of reacting the second reactive moiety under hydrogenolysis conditions or palladium catalyzed coupling conditions.

In some embodiments, the carboxaldehyde substituent is further reacted under reductive amination conditions to produce an aminomethyl substituted tetracycline compound; and the second reactive moiety is further reacted under palladium coupling conditions or under hydrogenolysis conditions. For example, the aminomethyl substituted tetracycline compound is a 7- or 9-aminomethyl substituted tetracycline compound.

The invention also relates to methods for synthesizing an aminomethyl substituted tetracycline compound comprising the steps of: a) reacting reactive tetracycline intermediate with carbon monoxide, a palladium catalyst, a phosphine ligand, a silane and a base under appropriate conditions, wherein the reactive tetracycline intermediate is substituted at a first position with a first reactive moiety and at a second position substituted with a second reactive moiety, wherein the first reactive moiety is replaced with a carboxaldehyde substituent; b) reacting the carboxaldehyde substituent under reductive amination conditions; and c) reacting the second reactive moiety under palladium coupling conditions or under hydrogenolysis conditions.

For example, the first reactive moiety is iodine and the second reactive moiety is bromine. In one embodiment, the reactive tetracycline intermediate is 7-bromo-9-iodosancycline. For example, the aminomethyl substituted tetracycline compound is a 7- or 9-aminomethyl substituted tetracycline compound.

In one embodiment, the method further comprises the step of precipitating the carboxaldehyde substituted tetracycline compound in a solvent, such as a non-polar solvent. Examples of non-polar solvents include diethyl ether, MBTE, heptane and combinations thereof.

In some embodiments, the method of the invention, further includes adding a Lewis acid with the carbon monoxide, the palladium catalyst, the phosphine ligand, the silane and the base. For example, the Lewis acid is $InCl_3$. In some embodiments, a Lewis acid is used in the presence of a trialkylamine base.

One example of a palladium catalyst is $Pd(OAc)_2$. One example of a phosphine ligand is a xantphos ligand, such as xantphos. Examples of the silane include $Ph_2SiH_2$ and $Et_3SiH$. Examples of the base include carbonate bases and trialkylamine bases. For example, the base can be sodium carbonate or diisopropylethylamine.

In various embodiments of the invention, the substituted tetracycline compound is synthesized in at least about 90% yield. In other examples, the substituted tetracycline compound is synthesized in about 91%, 92%, 93%, 94%, 95%, 96%, 97%, 98%, or 99% yield.

The invention generally pertains to methods for synthesizing substituted minocycline compounds. In one embodiment, the invention pertains, at least in part, to a method for synthesizing a carboxaldehyde substituted minocycline compound by reacting a minocycline reactive intermediate under appropriate conditions with carbon monoxide, a palladium catalyst, a silane and a base, such that the carboxaldehyde substituted minocycline compound is synthesized.

For example, the palladium catalyst is $PdCl_2(tBu_2PhP)_2$ dichlorobis(di-tert-butylphenylphosphine palladium (II)] or $PdCl_2$(DPEPhos) [bis(diphenylphosphinophenyl)ether palladium (II) chloride].

In one embodiment, the silane is $Et_3SiH$. In one embodiment, the base is a carbonate base, for example, sodium carbonate.

In one embodiment, the method further comprises the step of precipitating the carboxaldehyde substituted minocycline compound in a solvent, such as a non-polar solvent. Examples of non-polar solvents include diethyl ether, MBTE, heptane and combinations thereof.

For example, the minocycline reactive intermediate is a halogenated minocycline intermediate, such as an iodine substituted minocycline intermediate, a chlorine substituted minocycline intermediate, or a bromine substituted minocycline intermediate. For example, the compound is a 9-halogenated minocycline. One example is 9-iodo minocycline.

For example, the palladium catalyst is $PdCl_2(tBu_2PhP)_2$ dichlorobis(di-tert-butylphenylphosphine palladium (II)] or $PdCl_2$(DPEPhos) [bis(diphenylphosphinophenyl)ether palladium (II) chloride].

In one embodiment, the silane is $Et_3SiH$. In one embodiment, the base is a carbonate base, for example, sodium carbonate.

In yet another embodiment, the invention pertains, at least in part, to a method for synthesizing a substituted minocycline compound by reacting a carboxaldehyde substituted minocycline compound under palladium catalyzed coupling conditions, hydrogenolysis conditions or reductive amination conditions.

The invention also pertains, at least in part, to a method for synthesizing an aminomethyl substituted minocycline compound comprising the steps of: a) reacting a reactive minocycline intermediate with carbon monoxide, a palladium catalyst, a silane and a base under appropriate conditions, to form a carboxaldehyde substituted minocycline, and b) reacting the carboxaldehyde substituted minocycline under reductive amination conditions to form an aminomethyl substituted minocycline compound.

In one embodiment, the aminomethyl substituted minocycline compound is a 9-aminomethyl substituted minocycline compound.

For example, the palladium catalyst is $PdCl_2(tBu_2PhP)_2$ dichlorobis(di-tert-butylphenylphosphine palladium (II)] or $PdCl_2$(DPEPhos) [bis(diphenylphosphinophenyl)ether palladium (II) chloride].

In one embodiment, the silane is $Et_3SiH$. In one embodiment, the base is a carbonate base, for example, sodium carbonate.

In one embodiment, the method further comprises the step of precipitating the carboxaldehyde substituted minocycline compound in a solvent, such as a non-polar solvent. Examples of non-polar solvents include diethyl ether, MBTE, heptane and combinations thereof.

In one embodiment, the substituted minocycline compound is at least about 51% pure. For example, the substituted minocycline compound is about 55%, 60%, 65%, 69%, or 70% pure.

This invention identifies an efficient route for the synthesis of 9-amino-methyl-substituted minocyclines, such as, for example, Compound 1:

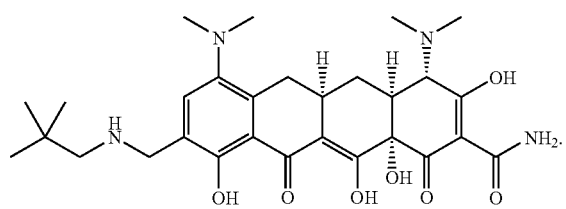 [SMILES: CN(C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O]

DETAILED DESCRIPTION OF THE INVENTION

The regioselective functionalization of the D-ring site in the tetracycline class of therapeutic agents has been a significant hurdle to overcome in the development of practical synthetic methodology. The chemical diversity that can be achieved through selective functionalization can have a major impact in the discovery of novel compounds of pharmaceutical interest. Conventional techniques in the installment of regioselective chemical "handles" on positions C7 and C9 of the D-ring of tetracyclines typically entail the use of temporary blocking groups or other functionality (e.g., a $NH_2$ group), which can have major drawbacks in terms of regioselectivity, yield and practicality. In that regard, the need for a methodology that can overcome these problems and complement well-established transformations would greatly benefit the development of new chemically diverse tetracycline compounds.

The advancement in the development of palladium coupling reactions has made a major impact on practical tetracycline derivatization, particularly at positions C7 and C9 on the D-ring. Practical large-scale carboxaldehyde functionalization of tetracyclines has been faced with significant hurdles as the current method is not conducive on a process scale. Since tetracycline compounds substituted with a carboxaldehyde at positions C7 and C9 are important intermediates in the synthesis of a broad scope of libraries, the need for an improved methodology that is conducive for a process scale is paramount. The traditional carbonylation of tetracyclines utilizes $Bu_3SnH$ as a reducing agent, but this methodology has significant drawbacks on a process scale and typically its use is avoided in the synthesis of pharmaceuticals. In that regard, developing processes that utilize alternative reducing reagents, palladium catalysts and additives that can overcome the inherent problems with tin based reagents is important.

The use of silicon based reducing reagents in palladium catalyzed carbonylations is a viable alternative to organotin reducing agents. In terms of cost, a silicon based reducing reagent is an attractive substitute for $Bu_3SnH$ and has proved to be satisfactory in carboxaldehyde formation with the tetracycline compounds. Using similar conditions as that of the $Bu_3SnH$ methodology, the desired carboxaldehyde tetracycline compounds may be obtained in high yields. The silicon based reducing agents display good qualities in comparison to $Bu_3SnH$ where the formation of the desired carboxaldehyde was highly favored over the premature reduced byproduct, which is observed to a significant extent in the $Bu_3SnH$ reaction. Moreover, the incidence of epimerization of position C4 has been a major problem in tetracycline derivatization and can have a profound effect in reducing the overall yield. The use of a chelating Lewis acid as an additive may prevent epimerization and exhibits protective effects.

The conventional aqueous workup in the $Bu_3SnH$ method typically results in some decomposition and rapid epimerization further compounding the deleterious effect in reducing the overall yield. Therefore, another improved development in the use of silicon based reducing agents compared to the traditional organotin methodology is in the ease of isolating the desired product in a non-polar solvent, thereby circumventing time consuming chromatography.

This new method for synthesizing substituted tetracyclines utilizes a less toxic reducing agent, as well as a low catalyst loading, and provides the product in desirable epimer purity and yield. The combination of improved yields, better toxicity profile and reduced labor costs should have a profound effect on the process scale synthesis of substituted tetracyclines.

An alternative reducing reagent was investigated that can overcome the inherent problems with tin based reagents. The easily accessible iodotetracyclines are substrates for conversion into tetracycline carboxaldehydes. Through the C10 triflate intermediate, the C10 position is transformed to a carboxaldehyde functionality using the same catalytic carbonylation reaction.

For example, the catalyst derived from $Pd(OAc)_2$ and the ligand xantphos are used in the formylation process with several common silanes. A variety of silicon reagents can be used under similar conditions as in the tin method, to produce the desired carboxaldehyde tetracycline in high yields with simple workup. The attribute of favored formation of the carboxaldehyde results in a significant improvement in the yield and the reaction times are shorter, which avoids epimerization of the desired product. The product can be easily isolated in acceptable purity by precipitating the product in a mixture MTBE and heptane. This work up avoids tedious filtration and chromatography, and aqueous workup results in less decomposition and epimerization than in the $Bu_3SnH$ method (thereby improving the yield). The combination of improved yields, better toxicity profile and reduced labor costs profoundly affect the process synthesis of carboxaldehyde tetracyclines.

A palladium catalyzed carbonylation reaction was performed on 9-iodominocycline, which resulted in high yield with little if any epimerization. A multitude of other carboxaldehyde tetracyclines can also be produced from the following iodotetracyclines, which include 7-iodosacycline, 9-iododoxycycline, 7-chloro-9-iodosancycline, 7-bromo-9-iodosancycline and other C7 and or C9 combination tetracyclines. In the 7-bromo-9-iodosancycline case, the C9 iodo group is regioselectively carbonylated where the C7 bromo group is unreactive under the indicated conditions. The reaction proceeds in excellent yield generating the 7-bromo-9-carboxaldehydesancycline compound, which is a useful intermediate in the preparation of a variety of novel compounds of pharmaceutical interest.

The invention generally pertains to methods of synthesizing substituted tetracycline compounds. In one embodiment, the invention pertains, at least in part, to a method for synthesizing a carboxaldehyde substituted tetracycline compound.

The invention generally pertains to methods of synthesizing substituted minocycline compounds. In one embodiment, the invention pertains, at least in part, to a method for synthesizing a carboxaldehyde substituted minocycline compound.

The term "tetracycline compound" includes substituted or unsubstituted tetracycline compounds or compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, minocycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

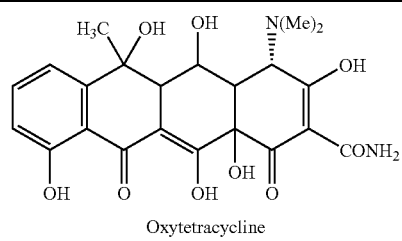

Oxytetracycline

TABLE 1-continued

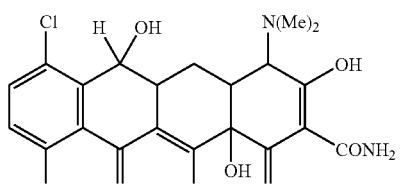
Demeclocycline

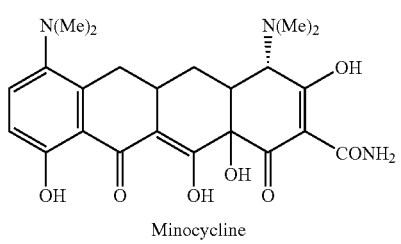
Minocycline

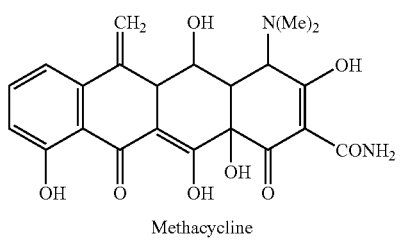
Methacycline

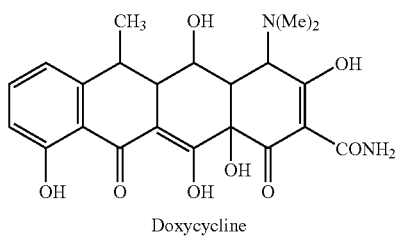
Doxycycline

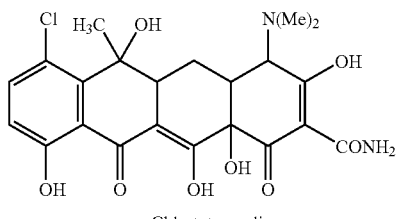
Chlortetracycline

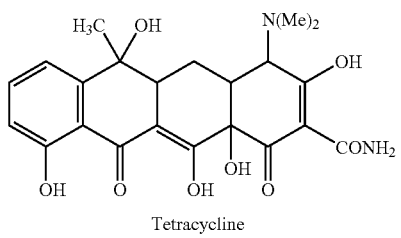
Tetracycline

TABLE 1-continued

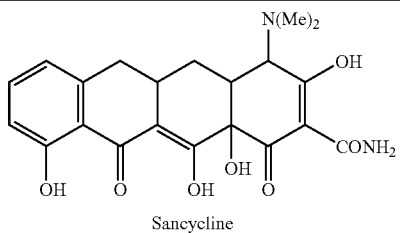
Sancycline

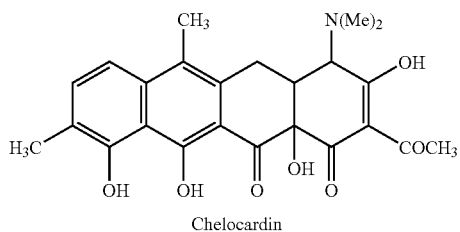
Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a,11a dehydro tetracyclines; 11a Cl-6,12 hemiketal tetracyclines; 11a Cl-6-methylene tetracyclines; 6,13 diol tetracyclines; 6-benzylthiomethylene tetracyclines; 7,11a-dichloro-6-fluoro-methyl-6-deoxy tetracyclines; 6-fluoro(α)-6-demethyl-6-deoxy tetracyclines; 6-fluoro(β)-6-demethyl-6-deoxy tetracyclines; 6-αacetoxy-6-demethyl tetracyclines; 6-βacetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

The term "substituted tetracycline compound" includes tetracycline compounds with one or more additional substituents, e.g., at the 1, 2, 3, 4, 5, 6, 7, 8, 9, 10, 11, 11a, 12, 12a or 13 position or at any other position which allows the substituted tetracycline compound of the invention to perform its intended function.

The term "carboxaldehyde substituted tetracycline compound" includes tetracycline compounds that are substituted with one or more aldehyde moieties (e.g. —C(O)H) at the 1, 2, 3, 4, 5, 6, 7, 8, 9, 10, 11, 11a, 12, 12a or 13 position or at any other position which allows the substituted tetracycline compound of the invention to perform its intended function. In one embodiment, the carboxaldehyde substituted tetracycline compound is a 7-, 9- and/or 10-carboxaldehyde substituted tetracycline compound.

In one embodiment, the invention pertains to methods for synthesizing a carboxaldehyde substituted tetracycline by reacting a tetracycline reactive intermediate under appropriate conditions. The term "appropriate conditions" includes any conditions that are suitable for carrying out the reaction of converting the tetracycline reactive intermediate to the carboxaldehyde substituted tetracycline. Appropriate conditions include any suitable solvents, temperature, catalysts and reagents. A skilled artisan would readily be able to determine appropriate conditions for carrying out the methods of the invention.

The term "tetracycline reactive intermediate" includes tetracycline compounds that are chemically reactive and undergo the desired reaction to form the substituted tetracycline compounds of the invention. In one embodiment, the tetracycline reactive intermediate is a halogenated tetracycline intermediate, including an iodine substituted tetracycline intermediate (e.g., 7-iodosancycline, 9-iododoxycycline), a chlorine substituted tetracycline intermediate, a bromine substituted tetracycline intermediate, an iodine and chlorine substituted tetracycline intermediate (e.g., 7-chloro-9-iodosancycline) or a bromine and iodine substituted tetracycline intermediate (e.g., 7-bromo-9-iodosancycline). In another embodiment, the tetracycline reactive intermediate is a triflate substituted tetracycline intermediate (e.g., a 10-triflate substituted tetracycline intermediate). The term triflate includes the trifluoromethanesulfonate moiety and has the structure $CF_3SO_3$—. In another embodiment, the tetracycline reactive intermediate is a halogenated minocycline intermediate, including an iodine, chlorine, or bromine substituted tetracycline intermediate (e.g., 9-iodominocycline).

In one embodiment, the invention pertains to methods for synthesizing a carboxaldehyde substituted tetracycline by reacting a tetracycline reactive intermediate under appropriate conditions with carbon monoxide, a palladium catalyst, a phosphine ligand, a silane and a base; such that the carboxaldehyde substituted tetracycline compound is synthesized.

In one embodiment, the invention pertains to methods for synthesizing a carboxaldehyde substituted tetracycline by reacting a tetracycline reactive intermediate under appropriate conditions with carbon monoxide, a palladium catalyst, a silane and a base; such that the carboxaldehyde substituted tetracycline compound is synthesized.

The term "palladium catalyst" includes palladium (II) chloride ($PdCl_2$), bis(acetonitrile)dichloropalladium, palladium (II) acetate ($Pd(OAc)_2$), 2-(dicyclohexylphosphino)biphenyl, [1,1'-bis(diphenylphosphino)ferrocene]dichloropalladium(II) complex, bis(triphenylphosphine)palladium (II) dichloride, dichlorobis(tricyclohexylphosphine) palladium(II), bis(triphenylphosphine)palladium(II) diacetate, tris(dibenzylideneacetone)dipalladium(0), allylpalladium chloride dimer, tetrakis(triphenylphosphine)palladium(0), bis[tris(4-(heptadecafluorooctyl)phenyl]phosphine]palladium(II) dichloride or bis[tris(3-(1H,1H,2H,2H-perfluorodecyl)phenyl)phosphine]palladium(II) dichloride. The term "palladium catalyst" also includes any palladium catalyst that may be suitable for catalyzing the conversion of the tetracycline reactive intermediate to the carboxaldehyde substituted tetracycline compound. In one particular embodiment, the palladium catalyst is palladium (II) acetate ($Pd(OAc)_2$).

The term "palladium catalyst" also includes phosphine-containing palladium (II) catalysts such as $PdCl_2(tBu_2PhP)_2$ dichlorobis(di-tert-butylphenylphosphine palladium (II)] and $PdCl_2(DPEPhos)$ [bis(diphenylphosphinophenyl)ether palladium (II) chloride]. The term "palladium catalyst" also includes any palladium catalyst that may be suitable for catalyzing the conversion of the minocycline reactive intermediate to the carboxaldehyde substituted minocycline compound.

The term "phosphine ligand" includes chelating non-chiral and chiral phosphine ligands that contain one or more phosphorus atoms trivalently bonded to an alkyl, alkenyl, alkynyl or aryl group. The term "phosphine ligand" also includes any phosphine ligand that may be suitable for use in the conversion of the tetracycline reactive intermediate to the carboxaldehyde substituted tetracycline compounds. In one embodiment, the phosphine ligand is a xantphos ligand. Examples of xantphos ligands are shown in Table 2. In one particular embodiment, the xantphos ligand is xantphos.

TABLE 2

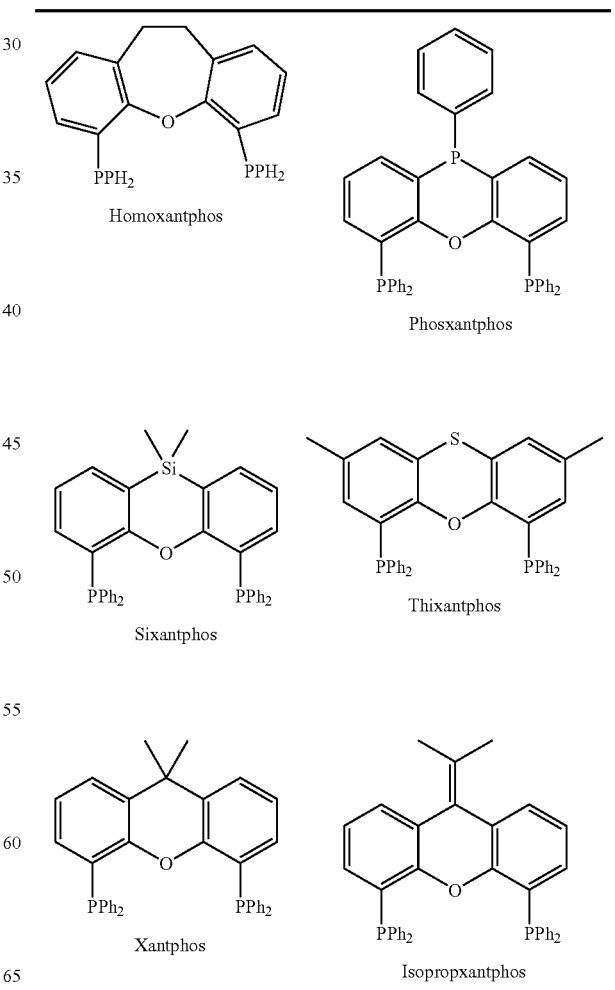

TABLE 2-continued

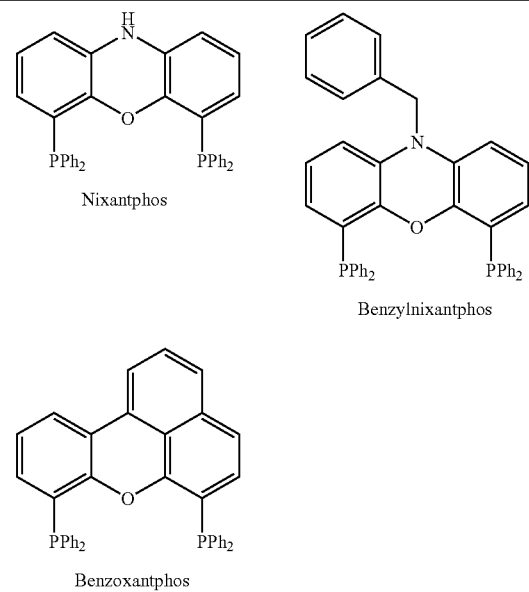

Nixantphos

Benzylnixantphos

Benzoxantphos

The term "silane" includes compounds with the chemical formula $R_2SiH_2$ or $R_3SiH$, in which each R is independently $C_1$-$C_{10}$ branched or straight chain alkyl or $C_5$-$C_{14}$ aryl. Examples of silanes include, for example, tripropylsilane ($Pr_3SiH$), triisopropylsilane ($iPr_3SiH$), benzyldimethylsilane, di-tert-butylsilane ($tBu_2SiH_2$), triethylsilane ($Et_3SiH$), cyclohexyldimethylsilane, dimethylphenylsilane, diethylisopropylsilane, methylphenylsilane, dimethylisopropylsilane, diethylmethylsilane, dimethylethylsilane, diethylsilane ($Et_2SiH_2$), trioctylsilane, dimethyloctadecylsilane, trihexylsilane, triphenylsilane ($Ph_3SiH$), diisopropyloctylsilane, methyldiphenylsilane, triisobutylsilane ($iBu_3SiH$), tributylsilane ($Bu_3SiH$), diphenylsilane ($Ph_2SiH_2$) and dimethylphenethylsilane. In one particular embodiment, the silane is $Ph_2SiH_2$ or $Et_3SiH$.

The term "base," includes chemical species that accept protons, such as carbonate bases and trialkylamines. Examples of carbonate bases include, for example, lithium carbonate, sodium carbonate, potassium carbonate, magnesium carbonate, calcium carbonate, strontium carbonate and lanthanum carbonate. In one embodiment, the carbonate base is sodium carbonate. Examples of trialkylamines include, for example, trimethylamine, triethylamine, tributylamine, triisopropylamine, dimethylethylamine, diisopropylethylamine, diethylmethylamine, dimethylisopropylamine and dimethylbutylamine. In one embodiment, the trialkylamine is diisopropylethylamine.

The invention also pertains, at least in part, to methods for synthesizing a substituted tetracycline compound by reacting the carboxaldehyde substituted tetracycline compound under palladium catalyzed coupling conditions, hydrogenolysis conditions or reductive amination conditions.

For example, the C9 position of 7-bromo-9-iodosancycline can be selectively converted to a carboxaldehyde group selectively in a palladium catalyzed reductive carbonylation reaction. The reaction has excellent regioselectivity where the C9 iodo group reacts preferentially with $Pd(PPh_3)_4$, $Bu_3SnH$, and CO in NMP at 70° C. The reaction proceeds in good yield generating the 7-bromo-9-carboxaldehydesancycline compound that is a useful intermediate in the preparation of a variety of novel compounds.

The 7-bromo-9-carboxaldehydesancycline compound can participate in a reductive alkylation reaction to furnish C9 position aminomethyl derivatives. In another sequence, the C7 bromo group can then either be reduced under hydrogenolysis or the bromo group can participate in a variety of palladium catalyzed coupling processes to afford a multitude of C7 functionalized, C9 aminomethyl sancycline derivatives.

In using palladium catalyzed coupling reactions, the C9 position can be selectively coupled with an appropriate regioselective catalyst to furnish a 9 position alkyl, aryl, heterocycle, carbonyl or other type of functional groups. As stated above, the C7 bromo group can either be reduced or coupled to generate a variety of C7 substituted sancycline derivatives. In subjecting the bromo group of a 7-bromo-9-carboxaldehydesancycline compound to a coupling process, a variety of C7 and C9 position combination substituted compounds can be produced.

In one embodiment, the invention pertains a method for synthesizing a 9-substituted minocycline compound by reacting a reactive minocycline intermediate with carbon monoxide, a palladium catalyst, a silane and a base under appropriate conditions, wherein the reactive minocycline intermediate is substituted at the 9-position with a reactive moiety such that the reactive moiety is replaced with a carboxaldehyde substituent.

The phrase "palladium catalyzed coupling conditions" refers to reaction conditions that include a palladium catalyst and converts a tetracycline compound of the invention to a substituted tetracycline compound by the formation of a carbon-carbon bond at the 7, 8, 9 and/or 10 position of the tetracycline compound or at any other position which allows the substituted tetracycline compound of the invention to perform its intended function. Examples of palladium catalyzed coupling conditions include reductive aminations, Stille reactions, Suzuki coupling reactions and Heck reactions. A skilled artisan would be able to readily determine other applicable palladium catalyzed coupling conditions for the conversion of a tetracycline compound of the invention to a substituted tetracycline compound. In one embodiment, the palladium catalyzed coupling conditions includes an organotin compound (e.g., $Bu_3SnR'$, wherein R' is a $C_1$-$C_{10}$ straight or branched chain alkyl, a $C_2$-$C_{10}$ branched or straight chain alkenyl or alkynyl, or a $C_5$-$C_{14}$ aryl group), a halogen or triflate substituted compound (e.g., a halogen substituted tetracycline compound or a triflate substituted tetracycline compound), a palladium catalyst (e.g., Pd/C, $Pd(PPh_3)_4$, $Pd(OAc)_2$ or $Pd_2(dba)_3$) and a solvent. In another embodiment, the palladium catalyzed coupling conditions include an alkene (e.g., $R^1C=CR^2$, wherein $R^1$ and $R^2$ are each independently hydrogen, a $C_1$-$C_{10}$ straight or branched chain alkyl, a $C_2$-$C_{10}$ branched or straight chain alkenyl or alkynyl, or a $C_5$-$C_{14}$ aryl group), a halogen or triflate substituted compound (e.g., aryl, benzyl, or vinyl halogen or triflate compound, such as, for example, a halogen substituted tetracycline compound or a triflate substituted tetracycline compound), a palladium catalyst (e.g., Pd/C, $Pd(PPh_3)_4$, $PdCl_2$ or $Pd(OAc)_2$), a phosphine ligand (e.g., triphenylphosphine or 2,2'-bis(diphenylphosphino)-1,1'-binaphthyl (BINAP)), a base (e.g., triethylamine, potassium carbonate or sodium acetate) and a solvent. In yet another embodiment, the palladium catalyzed coupling reaction includes an aryl or vinyl boronic acid (e.g., a compound of the formula $R^3B(OH)_2$ in which $R^3$ may be, for example, a $C_2$-$C_{10}$ branched or straight chain alkenyl or alkynyl, or a $C_5$-$C_{14}$ aryl group), an aryl or vinyl halide or triflate (e.g., a halide or triflate substituted $C_2$-$C_{10}$ branched or straight chain alkenyl, halide or triflate substituted $C_5$-$C_{14}$ aryl group or a halogen substituted tetracycline compound or a triflate substituted tetracycline compound), a palladium catalyst (e.g., Pd(PPh$_3$)$_4$) and a solvent.

The phrase "hydrogenolysis conditions" refers to reaction conditions that convert a tetracycline compound of the invention to a substituted tetracycline compound by the addition of a molecule of hydrogen at the 7, 8, 9 and/or 10 position of the tetracycline compound or at any other position which allows the substituted tetracycline compound of the invention to perform its intended function. A skilled artisan would be able to readily determine other applicable hydrogenolysis conditions for the conversion of a tetracycline compound of the invention to a substituted tetracycline compound. In one embodiment, hydrogenolysis conditions include a palladium catalyst (e.g., [1,1'-bis(diphenylphosphino)ferrocene]dichloropalladium(II) complex (Cl$_2$Pd (dppf))), an ammonium compound (e.g., ammonium formate) and one or more solvents (e.g., 1-methyl-2-pyrrolidinone (NMP) and water). In some examples, palladium on carbon (Pd/C) is the hydrogenolysis catalyst. In other examples, a borohydride agent is the hydrogenolysis catalyst.

The phrase "reductive amination conditions" refers to reaction conditions that involve the conversion of a carbonyl group (e.g., a carboxaldehyde moiety) to an amine at the 7, 8, 9 and/or 10 position of the tetracycline compound or at any other position which allows the substituted tetracycline compound of the invention to perform its intended function. A skilled artisan would be able to readily determine other applicable reductive amination conditions for the conversion of a tetracycline compound of the invention to a substituted tetracycline compound. In one embodiment, the reductive amination conditions include a reducing agent (e.g., sodium cyanoborohydride or sodium triacetate borohydride), a primary or secondary amine, wherein the amine is a $C_1$-$C_{10}$ branched or straight chain alkyl amine (e.g., methylamine, dimethylamine, ethylamine, diethylamine, isopropylamine, diisopropylamine, t-butylamine, propylamine, butylamine and the like) or $C_5$-$C_{14}$ aryl amine (e.g., phenylamine, diphenylamine and the like), and a solvent (e.g., dimethylformamide (DMF) or 1,2-dichloroethane). In some embodiments, the reductive amination is performed in the presence of Pd/C. In some reactions, Pd/C is not included in the reductive amination reaction.

In one embodiment, the invention pertains a method for synthesizing a substituted tetracycline compound by reacting a reactive tetracycline intermediate with carbon monoxide, a palladium catalyst, a phosphine ligand, a silane and a base under appropriate conditions, wherein the reactive tetracycline intermediate is substituted at a first position with a first reactive moiety and substituted at a second position with a second reactive moiety, such that one of the first reactive moiety is replaced with a carboxaldehyde substituent and the second reactive moiety is unreacted.

In one embodiment, the invention pertains a method for synthesizing a 9-substituted minocycline compound by reacting a reactive minocycline intermediate with carbon monoxide, a palladium catalyst, a silane and a base under appropriate conditions, wherein the reactive minocycline intermediate is substituted at the 9-position with a reactive moiety such that the reactive moiety is replaced with a carboxaldehyde substituent.

In one embodiment, the method for synthesizing substituted tetracycline compounds provides the desired substituted tetracycline compounds in high yield. For example, the yield is at least about 90%, at least about 91%, at least about 92%, at least about 93%, at least about 94%, at least about 95%, at least about 96%, at least about 97%, at least about 98%, or at least about 99%. In another embodiment, the desired substituted tetracycline is synthesized in about quantitative yields.

In one embodiment, the method for synthesizing substituted minocycline compounds provides the desired substituted tetracycline compounds in high yield. For example, the yield is at least about 90%, at least about 91%, at least about 92%, at least about 93%, at least about 94%, at least about 95%, at least about 96%, at least about 97%, at least about 98%, or at least about 99%. In another embodiment, the desired substituted tetracycline is synthesized in about quantitative yields.

In another embodiment, the invention pertains to a method for synthesizing an aminomethyl substituted tetracycline compound comprising the steps of: a) reacting a reactive tetracycline intermediate with carbon monoxide, a palladium catalyst, a silane and a base under appropriate conditions, wherein reactive tetracycline intermediate is substituted at the 9-position with a reactive moiety, wherein the reactive moiety is replaced with a carboxaldehyde substituent; b) reacting the carboxaldehyde substituent under reductive amination conditions.

For example, the aminomethyl substituted tetracycline compound is a 9-aminomethyl substituted minocycline compound.

In one embodiment, the 9-aminomethyl minocycline compound synthesized by the method of the invention is substantially pure. For example, the purity is greater than 50%, at least about 55%, at least about 60%, at least about 65%, at least about 69%, at least about 70%, at least about 75%, at least about 80%, at least about 85%, at least about 90%, or at least about 99%.

In yet another embodiment, the method for synthesizing the tetracycline compounds of the invention further comprises the step of precipitating the substituted tetracycline compound in a solvent, such as, for example, a non-polar solvent. The term "non-polar solvent" includes those solvents that have a dielectric constant of less than about 15. Examples of non-polar solvents include, for example, hexanes, heptane, benzene, toluene, diethyl ether (Et$_2$O), chloroform, ethyl acetate, dichloromethane and methyl t-butyl ether (MBTE, or TMBE) or combinations thereof. In one embodiment, the solvent is Et$_2$O, MBTE, heptane or a combination thereof.

This invention identifies an efficient route for the synthesis of 9-amino-methyl-substituted minocyclines, such as, for example, Compound 1:

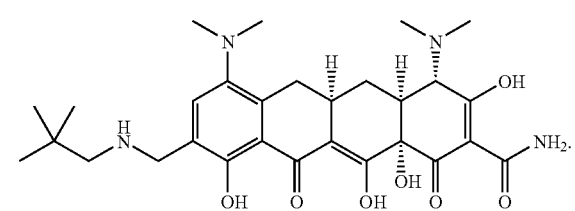 [SMILES: CN(C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O]

The method of the invention employs a selective palladium-phosphine catalyst, such as PdCl$_2$(tBu$_2$PhP)$_2$ or PdCl$_2$(DPEPhos) for converting the 9-iodo compound to the 9-formyl compound. This method results in a much higher and selective conversion of iodominocycline to formylminocycline relative to previously described syntheses. The high quality of the formylminocycline that is produced by these methods leads to corresponding improvement in the quality and yield of the subsequent reductive amination. The reductive amination can be performed with a variety of amines, for example, the neopentyl amine can be used to generate Compound 1.

In one embodiment, the substituted tetracycline compound is of formula (I):

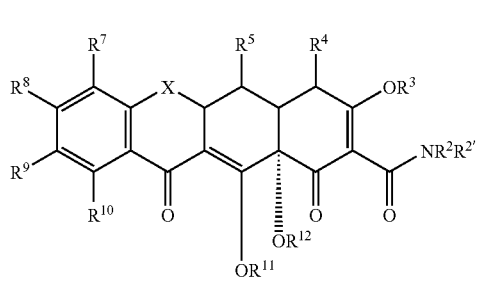

(I)

wherein:
X is CHC($R^{13}$Y'Y), C$R^{6'}R^6$, S, N$R^6$, or O;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is N$R^{4'}R^{4''}$, alkyl, alkenyl, alkynyl, hydroxyl, halogen, or hydrogen;
$R^3$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^8$ is alkyl, alkenyl, alkynyl, aryl, arylalkyl, arylalkenyl or arylalkynyl, formyl or carbonyl;
$R^7$ is alkyl, alkenyl, alkynyl, aryl, arylalkyl, arylalkenyl or arylalkynyl, formyl or carbonyl;
$R^9$ is alkyl, alkenyl, alkynyl, aryl, arylalkyl, arylalkenyl or arylalkynyl, formyl or carbonyl;
$R^{10}$ is hydroxyl, alkoxyl, alkyl, alkenyl, alkynyl, aryl, arylalkyl, arylalkenyl, arylalkynyl, formyl or carbonyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In another embodiment, the invention pertains to a method for synthesizing an aminomethyl substituted tetracycline compound comprising the steps of: a) reacting a reactive tetracycline intermediate with carbon monoxide, a palladium catalyst, a phosphine ligand, a silane and a base under appropriate conditions, wherein reactive tetracycline intermediate is substituted at a first position with a first reactive moiety and substituted at a second position with a second reactive moiety, wherein the first reactive moiety is replaced with a carboxaldehyde substituent; b) reacting the carboxaldehyde substituent under reductive amination conditions; and c) reacting the second reactive moiety under palladium coupling conditions or under hydrogenolysis conditions.

In one embodiment, the aminomethyl substituted tetracycline compound is a 9-aminomethyl substituted compound of formula (II):

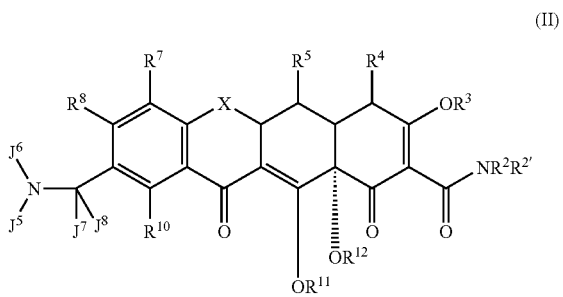

(II)

wherein:
$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;
$J^7$ and $J^8$ are each alkyl, halogen, or hydrogen;
X is CHC($R^{13}$Y'Y), C$R^{6'}R^6$, C=C$R^{6'}R^6$, S, N$R^6$, or O;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is N$R^{4'}R^{4''}$, alkyl, alkenyl, alkynyl, aryl, hydroxyl, halogen, or hydrogen;
$R^3$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^8$ is alkyl, alkenyl, alkynyl, aryl, arylalkyl, arylalkenyl or arylalkynyl, formyl or carbonyl;
$R^7$ is alkyl, alkenyl, alkynyl, aryl, arylalkyl, arylalkenyl or arylalkynyl, formyl or carbonyl;
$R^{10}$ is hydroxyl, alkoxyl, alkyl, alkenyl, alkynyl, aryl, arylalkyl, arylalkenyl, arylalkynyl, formyl or carbonyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In another embodiment, the aminomethyl substituted tetracycline compound is a 7-aminomethyl substituted compound of formula (III):

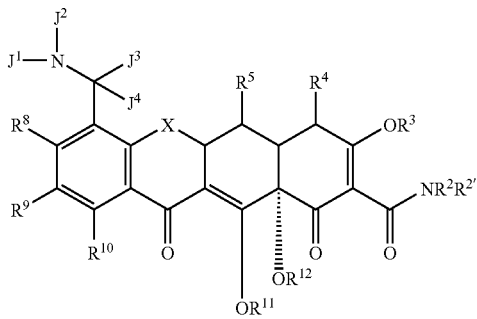

(III)

wherein:

$J^1$ and $J^2$ are each independently each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;

$J^3$ and $J^4$ are each alkyl, halogen, or hydrogen;

X is $CHC(R^{13}Y'Y)$, $CR^{6'}R^6$, $C=CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^3$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^8$ is alkyl, alkenyl, alkynyl, aryl, arylalkyl, arylalkenyl or arylalkynyl, formyl or carbonyl;

$R^9$ is alkyl, alkenyl, alkynyl, aryl, arylalkyl, arylalkenyl or arylalkynyl, formyl or carbonyl;

$R^{10}$ is hydroxyl, alkoxyl, alkyl, alkenyl, alkynyl, aryl, arylalkyl, arylalkenyl, arylalkynyl, formyl or carbonyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters, and prodrugs thereof.

Examples of the substituted tetracycline compounds that may be synthesized by the methods disclosed herein can be found in U.S. Pat. Nos. 6,818,634; 6,642,270; 6,500,812; 6,849,615; 6,818,635; 6,683,068; 6,846,939; 7,208,482; 7,001,918; 6,617,318; 7,067,681; 7,202,235; 6,833,365; 6,624,168 and 7,094,806; and U.S. Patent Publication Nos. 20040176334; 2006-0148765; 20050143353; 2007-0072834; 20040138183; 20040214801; 2005-0288262; 2006-0084634; 20040266740; 20050026875; 20050038002; 20050026876; 20050143352; 2006-0003971; 20050137174; 2006-0166945; 2006-0166944; 2006-0281717; 2007-0093455; 20040157807; 20050250744; 20050187198; 20050119235; 2006-0234988; 2006-0229282; 2006-0205698; the entire contents of each of these patents and patent applications are hereby incorporated by reference.

In one embodiment, the method for synthesizing the tetracycline compounds of the invention further comprises adding a Lewis acid with the carbon monoxide, the palladium catalyst, the phosphine ligand, the silane and a base. The term "Lewis acid" includes aluminum (III) bromide ($AlBr_3$), aluminum (III) chloride ($AlCl_3$), boron (III) chloride ($BCl_3$), boron (III) fluoride ($BF_3$), iron (III) bromide, iron (III) chloride, tin (IV) chloride ($SnCl_4$), titanium (IV) chloride ($TiCl_4$) or indium (III) chloride ($InCl_3$). In one embodiment, the Lewis acid is $InCl_3$. In another embodiment, the Lewis acid is used when the base is a trialkylamine (e.g., diisopropylethylamine).

In yet another embodiment, the method for synthesizing the tetracycline compounds of the invention further comprises the step of precipitating the substituted tetracycline compound in a solvent, such as, for example, a non-polar solvent. The term "non-polar solvent" includes those solvents that have a dielectric constant of less than about 15. Examples of non-polar solvents include, for example, hexanes, heptane, benzene, toluene, diethyl ether ($Et_2O$), chloroform, ethyl acetate, dichloromethane and methyl t-butyl ether (MBTE) or combinations thereof. In one embodiment, the solvent is $Et_2O$, MBTE, heptane or a combination thereof.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl(alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 10 or fewer carbon atoms in its backbone (e.g., $C_1$-$C_{10}$ for straight chain, $C_3$-$C_{10}$ for branched chain). The term $C_1$-$C_{10}$ includes alkyl groups containing 1 to 10 carbon atoms.

The term substituted alkyl includes alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl(alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 10 or fewer carbon atoms in its backbone (e.g., $C_2$-$C_{10}$ or straight chain, $C_3$-$C_{10}$ for branched chain). Likewise, cycloalkenyl groups may have from 3-10 carbon atoms in their ring structure. The term $C_2$-$C_{10}$ includes alkenyl groups containing 2 to 10 carbon atoms.

The term substituted alkenyl includes alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group.

The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc. The term "formyl" includes compounds with the formula —C(O)H.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

EXEMPLIFICATION OF THE INVENTION

Example 1

Preparation of 9-Carboxaldehydeminocycline

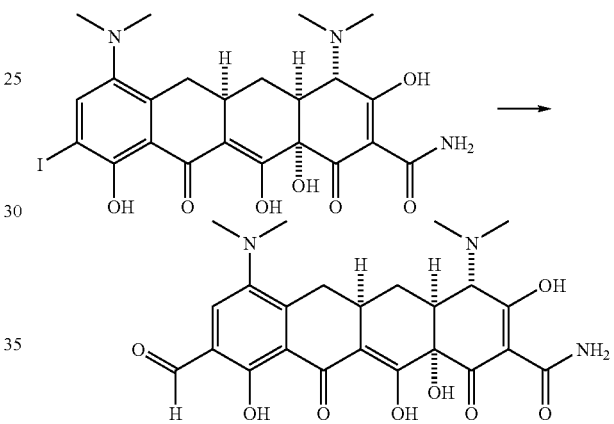

Method A.

A solution of anhydrous 9-iodominocycline freebase (14.6 g, 25.0 mmol), anhydrous InCl₃ (11.1 g, 50.0 mmol), anhydrous iPr₂NEt (8.73 mL, 50.0 mmol), Pd(OAc)₂ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et₃SiH (4.44 mL, 27.5 mmol) was added via syringe pump over a 90 minute period. After completion of reaction, the reaction was cooled to ambient temperature and diluted with CH₃CN (50 mL). The solution was transferred to another flask and while stirring vigorously Et₂O (approx. 500 mL) was added slowly to precipitate the product. The resulting suspension was collected on a fine fritted funnel rinsing with Et₂O. The product was further dried under high vacuum to afford 12.1 g in 99% yield.

Method B.

A solution of anhydrous 9-iodominocycline freebase (14.6 g, 25.0 mmol), anhydrous Na₂CO₃ (10.6 g, 100.0 mmol), Pd(OAc)₂ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et₃SiH (4.44 mL, 27.5 mmol) was added via syringe pump over a 90 minute period. After completion of reaction, the reaction was cooled to ambient temperature, diluted with CH₃CN (50 mL) and filtered through a fritted funnel. The solution was transferred to another flask and while stirring vigorously 1:1 MTBE/heptane (approx. 500 mL) was added slowly to precipitate the product. The resulting suspension was collected on a fine fritted funnel rinsing with 1:1 MTBE/heptane. The product was further dried under high vacuum to afford 12.1 g in 99% yield.

Example 2

Synthesis of 9-Carboxaldehydesancycline

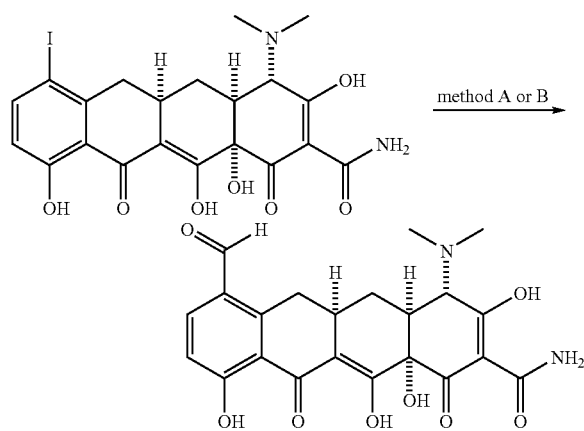

Method A.

To a solution of anhydrous 9-iodosancycline freebase (13.5 g, 25.0 mmol), Pd(OAc)₂ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et₃SiH (4.44 mL, 27.5 mmol) was added via syringe pump over a 90 minute period. After completion of reaction, the reaction was cooled to ambient temperature and diluted with CH₃CN (50 mL). The solution was transferred to another flask and while stirring vigorously Et₂O (approx. 500 mL) was added slowly to precipitate the product. The resulting suspension was collected on a fine fritted funnel rinsing with Et₂O. The product was further dried under high vacuum to afford 11.1 g in 99% yield.

Method B.

To a solution of anhydrous 9-iodosancycline freebase (13.5 g, 25.0 mmol), anhydrous Na₂CO₃ (10.6 g, 100.0 mmol), Pd(OAc)₂ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et₃SiH (4.44 mL, 27.5 mmol) was added via syringe pump over a 90 minute period. After completion of reaction, the reaction was cooled to ambient temperature, diluted with CH₃CN (50 mL) and filtered through a fritted funnel. The solution was transferred to another flask and while stirring vigorously 1:1 MTBE/heptane (approx. 500 mL) was added slowly to precipitate the product. The resulting suspension was collected on a fine fritted funnel rinsing with 1:1 MTBE/heptane. The product was further dried under high vacuum to afford 11.1 g in 99% yield.

Example 3

Preparation of 7-Bromo-9-Carboxaldehydesancycline

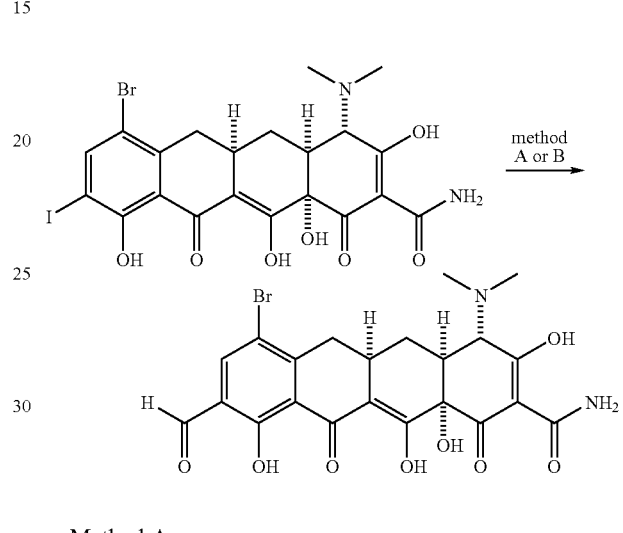

Method A.

A solution of anhydrous 7-bromo-9-iodosancycline freebase (15.5 g, 25.0 mmol), anhydrous InCl₃ (11.1 g, 50.0 mmol), anhydrous iPr₂NEt (8.73 mL, 50.0 mmol), Pd(OAc)₂ (0.11 g, 0.50 mmol) and xantphos (0.58 g, 1.00 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et₃SiH (4.44 mL, 27.5 mmol) was added via syringe pump over a 90 minute period. After completion of reaction, the reaction was cooled to ambient temperature and diluted with CH₃CN (50 mL). The solution was transferred to another flask and while stirring vigorously Et₂O (approx. 500 mL) was added slowly to precipitate the product. The resulting suspension was collected on a fine fritted funnel rinsing with Et₂O. The product was further dried under high vacuum to afford 13.0 g in 99% yield.

Method B.

To a solution of anhydrous 7-bromo-9-iodosancycline freebase (15.5 g, 25.0 mmol), anhydrous Na₂CO₃ (10.6 g, 100.0 mmol), Pd(OAc)₂ (0.11 g, 0.50 mmol) and xantphos (0.58 g, 1.00 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et₃SiH (4.44 mL, 27.5 mmol) was added via syringe pump over a 90 minute period. After completion of reaction, the reaction was cooled to ambient temperature, diluted with CH$_3$CN (50 mL) and filtered through a fritted funnel. The solution was transferred to another flask and while stirring vigorously 1:1 MTBE/heptane (approx. 500 mL) was added slowly to precipitate the product. The resulting suspension was collected on a fine fritted funnel rinsing with 1:1 MTBE/heptane. The product was further dried under high vacuum to afford 13.0 g in 99% yield.

Example 4

Preparation of 9-Aminomethylsancycline Derivatives

Example 5

Preparation of Compound 1

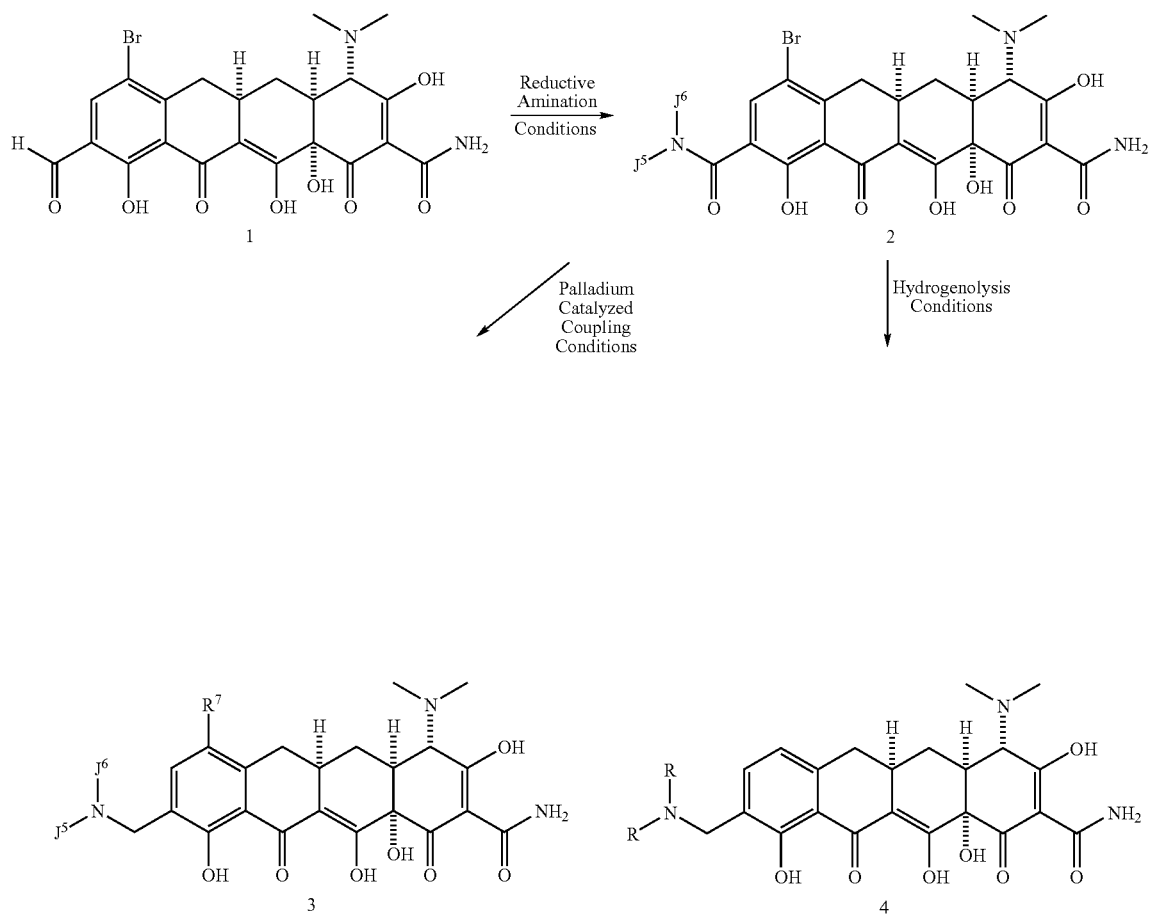

An amount of 9-carboxaldehyde-7-bromo tetracycline (1) is reacted under reductive amination conditions (e.g., a primary or secondary amine, DMF or 1,2-dichloroethane and NaCNBH$_3$ or NaBH(OAc)$_3$) to form a 9-aminomethyl-7-bromo tetracycline (2). The brominated intermediate is subjected to palladium catalyzed coupling conditions (an organotin reagent, a palladium catalyst and a solvent; an alkene, a palladium catalyst, a phosphine ligand and a base; or an aryl or vinyl boronic acid and a palladium catalyst) and a solvent to form 9-aminomethyl-7 substituted tetracycline compounds (3). Alternatively, the 9-aminomethyl-7-bromo tetracycline (2) can be subjected to hydrogenolysis conditions (e.g., a palladium catalyst, an ammonium formate and one or more solvents) to form 9-aminomethyl sancycline compounds.

-continued

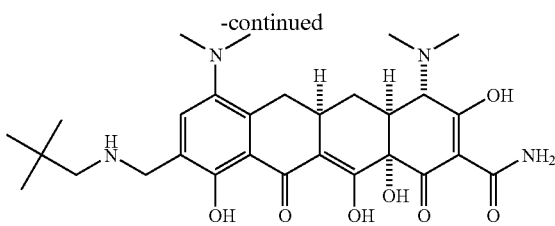

Method A Procedure for Preparation of 9-Carboxaldeminocycline

To a solution of anhydrous 9-iodominocycline freebase (14.6 g, 25.0 mmol), anhydrous InCl$_3$ (11.1 g, 50.0 mmol), anhydrous iPr$_2$NEt (8.73 mL, 50.0 mmol), Pd(OAc)$_2$ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et$_3$SiH (4.44 mL, 27.5 mmol) was added via syringe pump over a 90 min. period. After completion of reaction, the reaction was cooled to ambient temperature and diluted with CH$_3$CN (50 mL). The solution was transferred to another flask and while stirring vigorously Et$_2$O (approx. 500 mL) was added slowly to precipitate the product. The resulting suspension was collected on a fine fritted funnel rinsing with Et$_2$O. The product was further dried under high vacuum to afford 12.1 g in 99% yield.

Method B Procedure for the Preparation of 9-Carboxaldeminocycline

To a solution of anhydrous 9-iodominocycline freebase (14.6 g, 25.0 mmol), anhydrous Na$_2$CO$_3$ (10.6 g, 100.0 mmol), Pd(OAc)$_2$ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et$_3$SiH (4.44 mL, 27.5 mmol) was added via syringe pump over a 90 min. period. After completion of reaction, the reaction was cooled to ambient temperature, diluted with CH$_3$CN (50 mL) and filtered through a fritted funnel. The solution was transferred to another flask and while stirring vigorously 1:1 MTBE/heptane (approx. 500 mL) was added slowly to precipitate the product. The resulting suspension was collected on a fine fritted funnel rinsing with 1:1 MTBE/heptane. The product was further dried under high vacuum to afford 12.1 g in 99% yield.

Method A Procedure for the Preparation of 9-Carboxaldesancycline

To a solution of anhydrous 9-iodosancycline freebase (13.5 g, 25.0 mmol), Pd(OAc)$_2$ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et$_3$SiH (4.44 mL, 27.5 mmol) was added via syringe pump over a 90 min. period. After completion of reaction, the reaction was cooled to ambient temperature and diluted with CH$_3$CN (50 mL). The solution was transferred to another flask and while stirring vigorously Et$_2$O (approx. 500 mL) was added slowly to precipitate the product. The resulting suspension was collected on a fine fritted funnel rinsing with Et$_2$O. The product was further dried under high vacuum to afford 11.1 g in 99% yield.

Method B Procedure for the Preparation of 9-Carboxaldesancycline

To a solution of anhydrous 9-iodosancycline freebase (13.5 g, 25.0 mmol), anhydrous Na$_2$CO$_3$ (10.6 g, 100.0 mmol), Pd(OAc)$_2$ (0.11 g, 0.50 mmol) and xantphos (0.29 g, 0.50 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et$_3$SiH (4.44 mL, 27.5 mmol) was added via syringe pump over a 90 min. period. After completion of reaction, the reaction was cooled to ambient temperature, diluted with CH$_3$CN (50 mL) and filtered through a fritted funnel. The solution was transferred to another flask and while stirring vigorously 1:1 MTBE/heptane (approx. 500 mL) was added slowly to precipitate the product. The resulting suspension was collected on a fine fritted funnel rinsing with 1:1 MTBE/heptane. The product was further dried under high vacuum to afford 11.1 g in 99% yield.

Method A Procedure for the Preparation of 7-Bromo-9-Carboxaldesancycline

To a solution of anhydrous 7-bromo-9-iodosancycline freebase (15.5 g, 25.0 mmol), anhydrous InCl$_3$ (11.1 g, 50.0 mmol), anhydrous iPr$_2$NEt (8.73 mL, 50.0 mmol), Pd(OAc)$_2$. (0.11 g, 0.50 mmol) and xantphos (0.58 g, 1.00 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et$_3$SiH (4.44 mL, 27.5 mmol) was added via syringe pump over a 90 min. period. After completion of reaction, the reaction was cooled to ambient temperature and diluted with CH$_3$CN (50 mL). The solution was transferred to another flask and while stirring vigorously Et$_2$O (approx. 500 mL) was added slowly to precipitate the product. The resulting suspension was collected on a fine fritted funnel rinsing with Et$_2$O. The product was further dried under high vacuum to afford 13.0 g in 99% yield.

Method B Procedure for the Preparation of 7-Bromo-9-Carboxaldesancycline

To a solution of anhydrous 7-bromo-9-iodosancycline freebase (15.5 g, 25.0 mmol), anhydrous Na$_2$CO$_3$ (10.6 g, 100.0 mmol), Pd(OAc)$_2$ (0.11 g, 0.50 mmol) and xantphos (0.58 g, 1.00 mmol) in anhydrous NMP (100 mL) in a dried 3-neck flask with internal thermometer was purged with CO to saturate the solution, then a large balloon of carbon monoxide was affixed to the top of the flask to maintain a positive pressure. The solution was heated to obtain an internal temperature of 70° C. at which time Et$_3$SiH (4.44 mL, 27.5 mmol) was added via syringe pump over a 90 min. period. After completion of reaction, the reaction was cooled to ambient temperature, diluted with CH₃CN (50 mL) and filtered through a flitted funnel. The solution was transferred to another flask and while stirring vigorously 1:1 MTBE/heptane (approx. 500 mL) was added slowly to precipitate the product. The resulting suspension was collected on a fine fritted funnel rinsing with 1:1 MTBE/heptane. The product was further dried under high vacuum to afford 13.0 g in 99% yield.

Example 6

Alternate Preparation of Compound 1

9-Carboxaldehydeminocycline

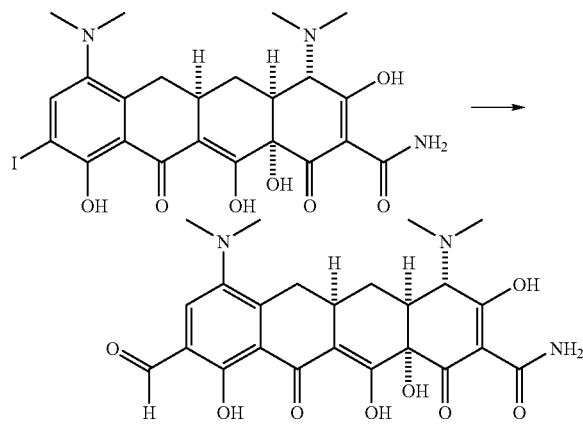

A 2 L pressure reactor equipped with heating mantle, mechanical stirring rod and stirrer bearing, temperature probe, addition funnel, condenser and gas manifold inlet valve was purged with CO (g). 625 mL 4/1 THF/DMF was charged to pressure reactor followed by 9-iodominocycline 70 g (120 mmol), Na₂CO₃ 24.18 g (228 mmol), and PdCl₂[tBu₂PhP]₂ 0.76 g (1.2 mmol) and stirred with heavy agitation. Triethylsilane 15.32 g (132 mmol) was charged to the addition funnel and the reaction mixture was purged with 30 psi CO (g) three times and then pressurized to 30 psi and heated to 70° C. while stirring. Once the temperature reached 70° C., the addition funnel was opened to allow triethylsilane addition dropwise over 2 hours and the reaction was stirred overnight at 70° C. under 30 psi CO (g).

Reaction completion was verified by LCMS and the reaction solution was allowed to gradually return to room temperature before filtering over a bed of celite. The celite cake was washed with 1000 mL THF and the filtrate was slowly added to 8000 mL TBME (tert butyl methyl ether) in a 12 L round bottom flask to precipitate crude 9-formylminocycline. The solution was stirred and chilled with an ice bath for 30 minutes before filtering. The filter cake was rinsed with 1000 mL TBME and then drip dried on a Buchner funnel with latex dental dam before drying in vacuum oven at room temperature overnight.

Preparation of 9-Aminomethylminocycline Derivatives

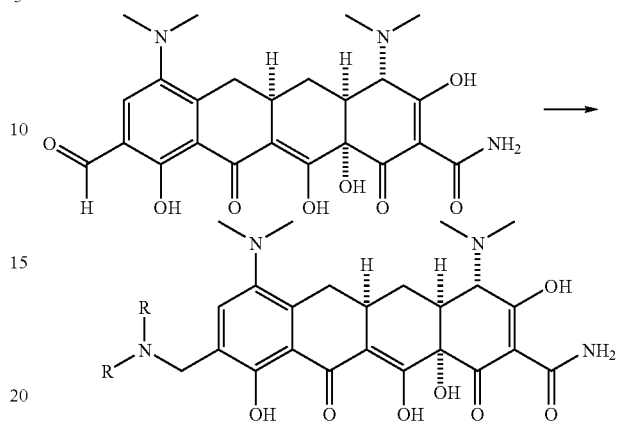

A mixture of 9-formylminocycline, neopentyl amine (9.34 mL), 5% Pd—C (Degussa E-196), wet (10 g) and methanol (100 mL) was hydrogenated at 30 psi in Paar shaker. After 18 hrs and a conversion of 13%, additional catalyst (5 g) was added and reaction was continued for another 24 hrs. After this time conversion was completed.

The reaction mixture was diluted with 10% Na₂SO₃ and filtered. The funnel was washed with MeOH and water giving totally 300 mL of filtrate.

The pH of filtrate was adjusted to 4.5 and extracted with dichloromethane (DCM) (2×100 mL) extracts were discarded and pH of water phase was brought to 7.5.

This solution was extracted again with DCM (4×180 mL) and the combined extracts were evaporated and dried to give yellow-greenish solid (5.41 g).

Part of this solid was redissolved in DCM and precipitated from TBME/pentane, filtered, dried and analyzed, purity (w/w %)=64.91%.

The application of this invention resulted in a yield of 59 g of crude Compound 1 from 100 g of minocycline compared to a yield of 44 g of crude from the corresponding input of minocycline in the known hydroxymethylphthalamide process. After correcting for assay the output of Compound 1 is 38 g compared to 22 g in the hydroxymethylphthalamide process.

The assay of the crude Compound 1 produced by this invention was 69% compared to 50% from the hydroxymethylphthalamide process.

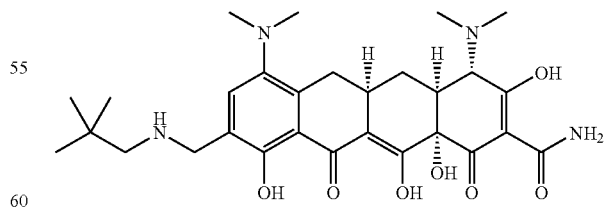

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for synthesizing a 9-substituted minocycline compound of the formula:

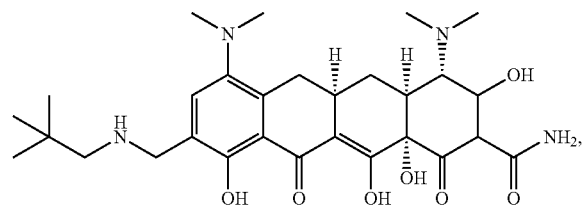 [SMILES: CN(C)c1cc(CNCC(C)(C)C)c(O)c2c1C[C@H]1C[C@H]3[C@H](N(C)C)C(O)C(C(N)=O)C(=O)[C@@]3(O)C(O)=C1C2=O]

comprising:
a) reacting a 9-halogenated minocycline with carbon monoxide, a first palladium catalyst, a silane and a base to generate a 9-carboxaldehyde substituted minocycline compound of the formula:

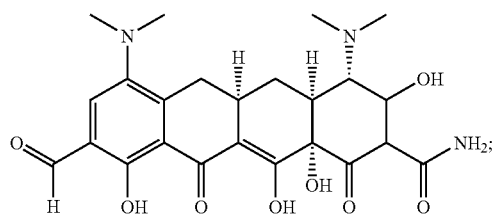 [SMILES: CN(C)c1cc(C=O)c(O)c2c1C[C@H]1C[C@H]3[C@H](N(C)C)C(O)C(C(N)=O)C(=O)[C@@]3(O)C(O)=C1C2=O]

and
b) reacting said 9-carboxaldehyde substituted minocycline compound with neopentyl amine under hydrogenolysis or reductive amination conditions to generate said 9-substituted minocycline compound of the formula:

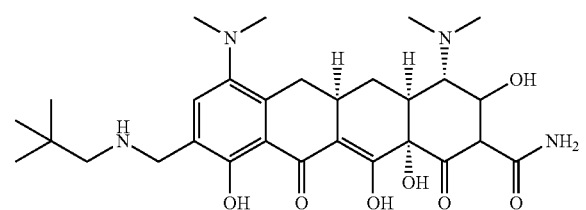 [SMILES: CN(C)c1cc(CNCC(C)(C)C)c(O)c2c1C[C@H]1C[C@H]3[C@H](N(C)C)C(O)C(C(N)=O)C(=O)[C@@]3(O)C(O)=C1C2=O]

or a pharmaceutically acceptable salt or ester thereof;
wherein said hydrogenolysis conditions comprise a second palladium catalyst, an ammonium compound and one or more solvents; and
wherein said reductive amination conditions comprise a reducing agent and a solvent.

2. The method of claim 1, wherein said 9-halogenated minocycline is a 9-iodine substituted minocycline, a 9-chlorine substituted minocycline, or a 9-bromine substituted minocycline.

3. The method of claim 1, wherein said first palladium catalyst is $Pd(OAc)_2$, $PdCl_2(tBu_2PhP)_2$ [dichlorobis(di-tert-butylphenylphosphine palladium (II)] or $PdCl_2(DPEPhos)$ [bis(diphenylphosphinophenyl)ether palladium (II) chloride].

4. The method of claim 1, wherein said first palladium catalyst is $Pd(OAc)_2$ or $PdCl_2(tBu_2PhP)_2$.

5. The method of claim 1, wherein said silane is triethylsilane.

6. The method of claim 1, wherein said base is sodium carbonate or diisopropylethylamine.

7. The method of claim 1, wherein said reaction in step a) comprises a solvent.

8. The method of claim 7, wherein said solvent is methylpyrrolidone or a mixture of tetrahydrofuran and dimethylformamide.

9. The method of claim 1, wherein said reaction in step a) comprises xantphos or $InCl_3$.

10. The method of claim 1, wherein said reductive amination conditions in step b) comprise methanol.

11. The method of claim 1, wherein:
step a) comprises:
a1) mixing 9-iodominocycline, sodium carbonate and $PdCl_2(tBu_2PhP)_2$ in a mixture of tetrahydrofuran and dimethylformamide in the presence of carbon monoxide;
a2) heating the mixture from a1);
a3) adding triethylsilane to the mixture from a2); and
a4) reacting the mixture from a3) such that a 9-carboxaldehyde substituted minocycline is generated; and
step b) comprises:
b1) hydrogenating said 9-carboxaldehyde substituted minocycline in the presence of neopentyl amine, 5% Pd—C, wet and methanol.

12. The method of claim 11, further comprising after a4) the following steps:
a5) filtering the reaction mixture from a4);
a6) adding the filtrate from a5) to tert-butyl-methyl-ether; and
a7) drying the precipitate from a6).

13. The method of claim 11, further comprising after b1) the following steps:
b2) diluting the mixture from b1) with sodium carbonate and filtering the mixture;
b3) adjusting the pH of the filtrate from b2);
b4) extracting the filtrate from b3) with dichloromethane; and
b5) drying the extracts from b4).

14. The method of claim 2, wherein said 9-halogenated minocycline is a 9-iodine substituted minocycline.

* * * * *